United States Patent [19]

Shade

[11] 4,281,149

[45] Jul. 28, 1981

[54] PROCESS FOR TREATING SILICON PARTICLES WITHIN A SILICONE REACTOR SYSTEM

[75] Inventor: Ray W. Shade, Clifton Park, N.Y.

[73] Assignee: General Electric Company, Waterford, N.Y.

[21] Appl. No.: 132,718

[22] Filed: Mar. 24, 1980

[51] Int. Cl.³ .............................. C07F 7/16; C07F 7/08
[52] U.S. Cl. ................................................... 556/472
[58] Field of Search ......................................... 556/472

[56] References Cited

U.S. PATENT DOCUMENTS

| 2,464,033 | 3/1949 | Gilliam | 556/472 |
| 2,466,412 | 4/1949 | Gilliam et al. | 556/472 |
| 2,466,413 | 4/1949 | Gilliam et al. | 556/472 |
| 3,133,109 | 5/1964 | Dotson | 556/472 |
| 3,536,743 | 10/1970 | Schrader et al. | 556/472 |
| 3,560,545 | 2/1971 | Schrader et al. | 556/472 |

Primary Examiner—Paul F. Shaver
Attorney, Agent, or Firm—E. Philip Koltos; John L. Young; Philip L. Schlamp

[57] ABSTRACT

A process for treating certain particles of less than 40 microns average diameter size in a silicone reactor where methyl chloride is reacted with particles of silicon in the presence of copper to produce chlorosilanes comprising removing particles of less than 40 microns average diameter size; and abraiding said particles to remove the surface coating; and returning said particles to the reactor.

29 Claims, 3 Drawing Figures

PROCESS FOR TREATING SILICON PARTICLES WITHIN A SILICONE REACTOR SYSTEM

BACKGROUND OF THE INVENTION

The present invention relates to the production of chlorosilanes and more particularly the present invention relates to processes for treating particles in a silicone reactor so as to make the particles usable for longer periods of time in a silicon reactor which is utilized for the production of chlorosilanes.

The present commercial method of manufacturing organosilanes is well-known and it is described in U.S. Pat. No. 2,380,995 Rochow. This patent discloses a direct reaction of an organohalide and more specifically methyl chloride with silicon particles with particles composed of silicon metal to produce organochlorosilanes. Intermixed with such particles of silicon matter that is intermixed with silicon particles there is intermixed particles of copper where copper in conjunction with silicon forms a reactive mass. In practice this reaction is generally carried out in one of three types of equipment: the stirred bed type of reactor as described in Sellers U.S. Pat. No. 2,449,821, the fluidized bed reactor described in Reed, et al U.S. Pat. No. 2,389,931 or a rotary kiln.

In the production of organochlorosilane by such a process the two basic products of the reaction are organotrichlorosilanes and diorganodichlorosilanes. Such compounds are utilized in the production of organopolysiloxane resins described in U.S. Pat. Nos. 2,258,218 to 2,258,222. Organopolysiloxane fluids described in U.S. Pat. Nos. 2,469,888 and 2,469,890 and the organopolysiloxane elastomers described in U.S. Pat. No. 2,448,756. The above patents are the early patents in the area. Since that time, there has been substantial innovations in the field and substantial patent literature has evolved on different types of compositions that can be produced from the basic organo chlorosilane. As pointed out previously, the basic products of such a reaction are organotrichlorosilane and diorganodichlorosilane. The diorganodichlorosilanes are preferred to be produced in high production since they can be utilized most widely, in particularly to produce linear polysiloxane fluids and polymers for the production of heat cured rubber elastomers and room temperature vulcanizable silicone rubber compositions elastomers of various types. Along with these organochlorosilanes there are produced minor amounts of other organochlorosilanes, however, these are not as important as the diorganodichlorosilanes. The amount of organotrichlorosilane is desired to be kept to a minimum in the chlorosilane production as discussed above. The only use of the organotrichlorosilane is to produce branch-chained fluids and certain resins. The excess of such organotrichlorosilane has to be converted to other types of organochlorosilanes before they can be utilized in silicone production. Accordingly, it is preferred in the production of organochlorosilanes by the direct process of Rochow that the weight ratio of triorganochlorosilane to diorganochlorosilane that the weight ratio of these two materials be about 0.1 during the production of chlorosilanes by the Rochow process and preferably not exceed the 0.35 level. However, it has been found in most manufacturing operations that what will happen is that the ratio will stay about the 0.15 level when the reactor is started up with new material and after a period raise to in excess of the 0.2 level. In the early times when this happened, the old silicon particles and the copper catalyst in the reactor would be removed and new particles would be inserted to the reactor and the reaction restarted. However, this was costly in terms of manufacturing cost.

Accordingly, there was always research being carried out as to determine how to more fully utilize the silicon particles in the reactor such that the weight ratio of organotrichlorosilanes to diorganochlorosilanes could be maintained at the desired level for a longer period of time resulting in the maximum utilization of the silicon particles to produce diorganodichlorosilanes. One of the breakthroughs in this area is for instance disclosed in U.S. Pat. No. 3,133,109 Dotson which is hereby incorporated by reference. Dotson disclosed that fuller use of the silicone particles could be carried out in that the amount of diorganodichlorosilane is maximized with respect to the organotrichlorosilane by passing used particles as they were utilized in the fluid bed reactor through an external fluid energy mill. As an alternative to the external fluid energy mill, Dotson also disclosed the passing of the used silicone particles that is particles that were recycled from the reactor through a plurality of sonic jets located at the base of the reactor wherein the silicon copper particles and organic chloride was passed through the jets at near sonic velocity to create a comminution of the particles or the breaking up of the silicon particles as a result of the particles striking each other or the walls of the reactor.

In one aspect of such construction, the jets have been designed so that they can face each other at the bottom of a fluid bed reactor and the particles, in accordance, with Dotson disclosure are made to strike each other in portions of the lower parts of the fluid bed reactor construction side so as to be comminuted or to be broken up into smaller particles. However, it was found by utilizing such a method that from the same amount of silicon particles, a larger amount of diorganodichlorosilane could be produced where the ratio of diorganodichlorosilane could be kept near the desired 0.15 or less than 0.35 value and more generally at the less than 0.35 value for a longer period of time. Utilizing the Dotson process 12 to 15% of the silicon that was introduced in the reactor was never utilized to produce an organochlorosilanes and removed as waste silicon from the process. Utilizing the Dotson process it was generally considered that said silicon was poisoned and was no longer capable of being utilized to produce diorganodichlorosilanes. Accordingly, it was highly unexpected that these fines or fine particles located in the fluid bed reactor of Dotson could be taken and treated so that they could be reutilized to produce diorganodichlorosilanes such that the ratio of organotrichlorosilanes did not exceed 0.35 for a longer period of time and such that the amounts of silicon metal lost as waste from the overall process would be reduced to less than 8%.

Accordingly, it is one object of the present invention to provide a process for treating the used silicon particles in a silicon reactor so that they may be activated to produce diorganodichlorosilanes.

It is another object of the present invention to provide a process for treating the used silicon particles in a silicon ractor for producing organochlorosilanes where the particles can be utilized for longer period of time to produce diorganodichlorosilanes with the weight ratio of organotrichlorosilanes and diorganodichlorosilanes will not exceed the 0.35 level for longer period of time that was possible prior to the present invention.

It is still another object of the present invention to provide a process for treating used silicon particles from a silicon fluidized bed reactor is that the overall loss of silicon as waste from the reactor process does not exceed 8%.

It is still another object of the present invention to provide a process for abraiding used silicon copper alloy particles from a fluid bed silicon reactor for the production of organochlorosilanes so as to remove the surface coating of such particles so that such particles can be reutilized in a reactor to produce organochlorosilanes.

These and other objects of the present invention are accomplished by means of the disclosure as set forth herein and below.

SUMMARY OF THE INVENTION

There is provided a process for treating the silicon particles in a silicon reactor for the production of organochlorosilanes where an organo chloride is reacted with particles of silicon in the presence of particles of copper to produce organochlorosilanes comprising (a) removing particles selected from particles of silicon and copper of less than 40 microns average diameter size from said reactor and abraiding said particles to remove the surface coating of such particles and returning said particles to the reactor to be utilized in the organochlorosilane reaction of the reactor. It should be noted that this treatment of particles can be utilized in any of the three reactors, a fluid bed reactor, which is the most widely utilized, a stirred reactor or a rotary kiln. Most preferably it is utilized in a fluid bed reactor. It is important to note that by the present process and by abraiding it is meant to disclose the removal of the surface of used or spent particles of silicon copper particles. It is not meant to include or comprise within the terms, communinution, or breaking up of the particles as a fracture of the total particle. What is meant is the fraction of the coating of the particles so as to remove the coating. This is what is meant by the term of abraiding. It is to distinguish from the comminuting of the Dotson process. By the utilization of this process, the silicon particles or silicon fines, that is, silicon particles or particles of silicon and copper of less than 40 microns in size or less than 40 microns average diameter size may be utilized for a longer period of time such that the amount of waste silicone materials that is removed from the reactor and dumped as waste is reduced to less than 8% by weight and is as low in some as cases as 5% by weight. The nature of the invention will be described herein and below.

DESCRIPTION OF THE PREFERRED EMBODIMENT

The organic halides which react with silicon in the process of the present invention have the formula:

RCl  (1)

where R is a monovalent organic radical, such as a hydrocarbon radical selected from the class consisting of alkyl radicals, e.g., methyl, ethyl, propyl, butyl, octyl, etc. radicals; aryl radicals, eg., phenyl, naphthyl, tolyl, xyly, etc. radicals; aralkyl radicals, e.g., phenylethyl, benzyl, etc. radicals; alkenyl radicals, e.g., vinyl, allyl, etc. radicals; alkynyl radicals, e.g., ethynyl, propynyl, etc. radicals; cycloalkyl radicals, e.g., cyclohexyl, cycloheptyl, etc. radicals; and cycloalkenyl radicals, e.g., cyclohepteny, cyclohexenyl radicals, etc. Among the preferred organic chlorides within the scope of Formula 1 can be mentioned for example, chlorobenzene, methyl chloride and ethyl chloride, with the preferred specific organic chloride being methyl chloride.

When the organic chloride of Formula 1 reacts with elemental silicon, the products formed consist primarily or organochlorosilanes having the formula:

$R_n SiCl_{4-n}$  (2)

where R is as previously defined and n is an integer equal to from 1 to 3. Specific examples of organochlorosilanes include methyltrichlorosilane, dimethyldichlorosilane and trimethylchlorosilane which are formed from methyl chloride; phenyltrichlorosilane, diphenyldichlorosilane and triphenylchlorosilane which are formed from chlorobenzene; and various other organochlorosilanes such as diethyldichlorosilane, dibenzyldichlorosilane, vinyltrichlorosilane, etc. which are formed from the appropriate organic chloride.

The elemental silicon with which the organic chloride reacts is in finely divided form and for optimum results, the silicon in the reactor has an average particle diameter in the range of from about 20 to 200 microns. Preferably at least 25 percent by weight of the silicon particles have actual diameters in the range of from 20 to 200 microns. While the reaction will proceed in the absence of a catalyst, it is preferred that the powdered silicon be mixed with powdered copper as taught in the aforementioned U.S. Pat. No. 2,380,995—Rochow. The powdered copper acts as a catalyst for increasing the rate of reaction between the organic chloride and the silicon. When copper powder is employed, the copper is present in the range of from about 0.5 to 20 percent, and preferably from about 2 to 10 percent, by weight, based on the weight of the finely divided silicon. One form of copper powder catalyst useful in the practice of the present invention is the powdered copper partially coated with copper oxide which is described in U.S. Pat. No. 2,443,902—Ferguson et al. and which has an average particle size in the range of about 1 to 20, and preferably 1 to 10, microns. In addition to the use of a catalyst such as copper, a promoter such as zinc metal, as taught in U.S. Pat. No. 2,464,033—Gilliam, can also be employed with the silicon and copper. Where such a promoter is employed, it is used preferably in amounts equal to from about 0.05 to 0.5 percent based on the weight of silicon.

As pointed out previously, it is important in the reaction of the instant case in the reactor where the organochlorosilanes are produced to maintain T/D ratio as hereinafter will be referred to which is the ratio in the product of the organotrichlorosilane to diorganichlorosilanes in the product stream coming from the reactor to as low as value as possible. Usually such value of the T/D ratio begins at the level of 0.25 increases and then as the reaction proceeds with fresh silicone or fresh copper particles, the T/D ratio drops to 0.1 to 0.2 where it stays for a long period of time and then slowly increases to above 0.2 and the higher values unless it is retarded. Usually the method of retarding the increase of the T/D of weight ratio is to insert or replace the spent or used silicon particles and silicon-copper particles in the reactor with new silicon particles and new silicon-copper particles.

Dotson found, for instance in the patent mentioned previously, that the T/D ratio could be maintained for a longer period of time at the level of below 0.35 by communiting the particles of silicon in the reactor to a smaller particles utilizing a fluid energy mill external to the reactor that is passing the particles to outside of the reactor and passing them through a fluid energy mill and then passing them back to the reactor after they have been comminuted. Another method was by the utilization of sonic jets in the reactor to communite the particles in situ as pointed out in the patent.

By communiting Dotson refers to the communition of grinding including such terms as crushing, pulverizing, disintegration and will include breakage of individual particles of the silicone copper mixture from compression, impact, or attition. However, it was found even with the use of the fluid energy mill or the jet mill internal to the reactor that nevertheless, even though the T/D ratio would be maintained below 0.35 for a longer period time, nevertheless, after a time the ratio would increase above that level. The terminology was commonly employed that at that point the silicon particles of size less than 40 microns average diameter were poisoned and there were to be dumped or disposed of in some way or another and fresh silicon and copper particles were inserted into the reactor to take the place of such silicon fines (for identification purposes in this patent application and in the claims and hereinafter, the terms "fines" shall include all silicon and silicon-copper particles of less than 40 microns average diameter in size. It should be noted that such silicon copper fines were not comminuted by the jet mill of the Dotson patent, that is the jet mill located at the bottom of the reactor of the Dotson patent. The reason for this was two-fold. Dotson disclosed that silicon particles could be comminuted by being passed through a jet mill or a fluid energy mill and more preferably through a jet mill at the bottom of the reactor, such that the T/D ratio could be maintained at a low level for a longer period time and wherein the silicon particles could be useable for the production of diorganodichlorosilane for a longer period of time. However, Dotson failed to appreciate that particles of 40 microns or less in average diameter would not be communuted or subjected to the communution process of his patent. It was found by experiment that even with the jets at the bottom of the reactor facing each other, particles of 40 microns or less average diameter would not have enough momentum such when they were collided with each other or with the side of the reactor would be comminuted and further it was found that particles of 40 microns or less would generally follow the stream path of the gases passing through the jet mill and would flow upwards along the part of the gas up through the reactor without striking each other with very much force or without striking each other at all. It was only the coarser particles that had the momentum to break the path of the upward flow of the gases and fly at each other so as to be comminuted or fly against the reactor wall so as to be comminuted.

Accordingly, when the silicon copper particle mixture in the reactor have been used for some time and had been comminuted and the T/D ratio went beyond permissible levels it was decided that the silicon copper particles in the reactor had become poisoned and they were dumped. The new virgin silicon coarser particles were inserted into the reactor. Dotson did not understand the reason why his silicon particles needed to be comminuted after they had been used in the process for some time and why the comminution maintained or dropped to the T/D ratio to a low level for a longer period of time. Other workers skilled in the art did not know why the silicon copper mixture became poisoned even after it had been used for a period of time and there was much speculation and work in the field.

It was only in the present case in which the instant inventor discovered that the poisoning effect that was evident of small and large particles of silicon and silicon-copper materials and reactors was not an effect that prevaded through out the entire body of the particles, but was a surface effect. It was discovered that this poisoning in fact was probably the result of the formation of a carbon contaminant on the surface of the particle which prevented further reaction of the organo chloride with the silicon metal to produce a sizable amount of diorganodichlorosilane as compared to organotrichlorosilane. Accordingly, it was found that the method of Dotson which worked to a certain degree that there would be lost from the silicon reactor 12 to 15% of silicon which would be dumped after it has been used as spent silicon materials. Accordingly, because of the ever increasing price of silicon metal, it was highly desirable to be able to utilize even more of the silicon in the spent silicon particles so that higher utilization of necessary raw material could be made. However, it was found that the jet mill disclosed in the Dotson patent was effective for comminuting particles only of about 40 microns or more in average diameter and were not effective in comminuting or destroying particles of less than 40 microns average diameter. It was found by experiment that the poisoned material on such particles of less than 40 microns was a surface phenomena and that the surface coating of the particle could be removed and the particles could be utilized to producing additional chlorosilanes in a reactor without the T/D ratio going above the maximum level. The process involving the grinding, crushing, pulverizing, and complete disintegration of the particles are difficult to apply on such small particles. Accordingly, it was unexpectedly found that a certain type of an abraiding technique could be utilized to remove the surface of such silicone fines, that is particles in a reactor of less than 40 microns average diameter in size by abraiding in this patent application "abraiding" means to rub or wear away a surface so as to leave the underlying surface exposed. It does not necessarily include crushing, or pulverizing of the material. It should be noted that maybe solvents could be utilized to remove the poisoned surface alloy in the particles; however, the problem with solvents is that there would be residual solvent left in the particles when they were returned to the reactor which would result in the production of unnecessary by-products in the reactor. Accordingly, solvents are not preferably utilized to remove or abraid the surface of the silicon fines or the silicon particles of average diameter size of less than 40 microns average diameter. The preferred method of removing the coatings on the silicon fines so that they can be recycled or returned to the reactor for further use in the production of organo chlorosilanes is mechanical abraiding technique wherein by a process where the surface of a particle is rubbed so as to remove the poisoned coating to leave exposed underneath the virgin silicon and copper material for utilization in the basic process for forming organochlorosilanes. There are many ways in which this mechanical abrasion can be carried out.

To abraid the surface of small particles it is necessary to have motion between two or more particles while the particles are in direct contact. Also the greater force tending to push the particles together the more effective is the abraiding action.

Thus, the three key factors in abrasion are (1) direct physical contact, (2) relative motion while in contact, (3) a force with a component perpendicular to the direct of relative motion. To assist in the abrasion of the surfaces of a sample of fine particles it may be advantageous to add a second material in particle form which has many sharp edges and is as hard as or harder than the surface of the first material fine particles. The ideal material to service this purpose in the present case is fresh ground virgin silicon since the combined materials may then be introduced into the reactor without further operation.

There are a number of ways this mechanical abrasion can be carried out. One preferred method is by introducing the fine silicon-copper powder into a rotating horizontal cylinder together with at least an equal weight of ground virgin silicon. As the cylinder rotates the particles of the intermixed material are subject to relative motion under the force exerted by the mass above that point. Rakes or baffles may be attached to the wall of the cylinder to enhance the extent of the particle-particle action. Alternately, balls, as used in ball milling, may be added to increase the load (or force) on the particles and thus accelerate the abrasion process. The surface abrasion should be accomplished more rapidly than the usual grinding that occurs in ball milling. The intent is to abraid not grind so the weight of the balls and the time for the grinding should be adjusted accordingly.)

Another alternate method is to combine the silicon-copper fines and freshly ground silicon in a horizontal cylinder which has a series of rakes paddes on blades that rotate on a drive shaft through the axis of the cylinder. As these rakes rotate they pass through the intermixed materials and cause relative motion between particles and effect surface abrasion.

Another alternate method is to pass a blend of the silicon-copper fines with the freshly ground silicon through a screw conveyor. The rotation of the screw forces the particles along the axis of the cylinder and simultaneously causes particle-particle motion and abrasion.

The action which the silicon-copper particles undergo in the cyclones, in falling into the receiving hopper, being dropped into the transfer hopper, transferred to a holding hopper, transferred to the feed hopper where they are blended with fresh silicon, and finally transferred to the reactor all contribute in varying degrees the removal of contaminant coatings on the particle surface.

It should be recognized that the presence of fresh ground silicon is not required to achieve the abraiding action but accelerates the rate at which the coating is removed from the silicon-copper particles surfaces.

An another alternative reaction powder may be used in place of freshly ground silicon to assist in the abraiding process.

Any apparatus that is designed to give particle-to-particle relative motion while the particles are in direct physical contact under a force pushing them together may be used to achieve the surface abrasion discussed here.

The ball milling process is preferred since it is effective and it requires inexpensive equipment to insert into the process for recycling the silicone fines.

As stated previously, the apparatus is simple and inexpensive and accomplishes the purpose admirably. It should be noted that any of the abraiding treatment processes can be carried out in an moisture free-atmosphere of air, they do not need to be carried out in an oxygen-free atmosphere as was the case with the comminuting of the Dotson patent. It should also be noted that such abraiding processes and treatments are preferably carried out in oxygen-free atmosphere.

It is preferred that if the abraiding is to be carried out at elevated temperatures that the atmosphere be oxygen-free. It should also be noted that this is the preferably process of abraiding. It should be noted, also, that in such ball mill procedures and other abraiding techniques that there will be some pulverization and crushing of particles; however, this will diminish as the size of the particles decrease below 40 microns in diameter and will be only a minimum phenomenon. In the ball milling of such particles, they will abraid against each other rubbing the surfaces of the particles or abraiding the surface of the particles to expose the virgin silicon metal beneath. This is true of also the other abrasion treatment techniques disclosed above. Accordingly, although there may become comminuting of the particles, especially the large particles of silicon and the silicon, copper fines, by the abraiding process disclosed; the particles are so small the basic effect of the instant process will be to abraid or rub off the surface of the particles so as to expose the new silicon material beneath the surface for further reaction to produce organo chlorosilanes.

It should also be noted that some of the very fine particles of 2.5 or 3 microns in size will go out with a product and as such will not be exposed to the process. Some of the fines below 2.5 or 3 microns in size may go out with the product and as such may not be exposed to the process of the instant case. However, it is also true that even such fine particles were retained, there would be questioned whether they would be abraided by any known commercial method. However, such very fines particles or fines of less than 5 or 7 microns in size constitute a very small portion of the total silicon and silicon copper particles in the reactor. The silicon fines and the silicon-copper fines from the reactor may be also be abraided by another method which is a new method for separating out the fines and tumbling them from one transfer hopper to another so that the surface of the particles are abraided off and the particles can be used as additional particles of copper and copper, silicon in the reactor that is they can be recycled after treatment into a reactor to be utilized as additional particles of copper and copper and silicon to produce organochlorosilanes. By such a process as will be disclosed below it is possible to increase the use of the virgin silicon that goes into the reactor such that there is a waste of 8% or less of silicon lost as wasted silicon in the fines or particles that are dumped as poisoned or spent from the reactor.

Figure 1:
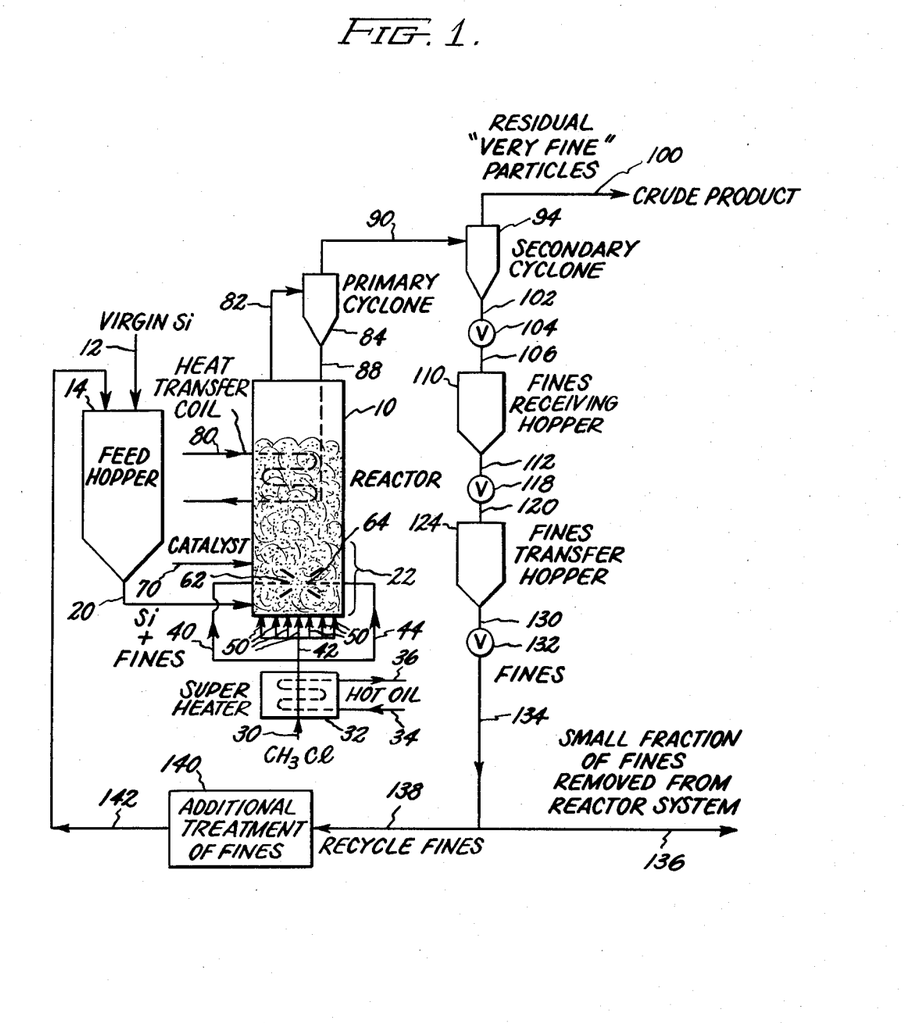
FIG. 1 is a schematic diagram of the process of the instant case as applied to one reactor.

Proceeding to FIG. 1. FIG. 1 is a preferred process of the instant case as applied to a single reactor. FIG. 1 contains silicone reactor 10. Virgin silicon material is feed through line 12 into feed hopper 14. Such virgin silicon material is in the form of silicon particles of an average particle diameter of anywhere from less than 20 to greater than 300 microns in average diameter. The mean particle size is 100 to 150 microns in diameter. The silicone particles pass from feed hopper 14 to line 20 to the bottom portion of 22 of reactor 10. Methyl chloride is passed from a supply tank to line 30 into super heater 32 which is heated by hot oil passing through lines 34 and 36. The methyl chloride or any organo chlorosilane used in the reactor is preferably heated to temperature of anywhere from 250° to 300° C. Organic chloride then passes out of heater 32 into three lines 40, 42, 44. Then the methyl chloride in line 42 passes through jets in combination 50 at the bottom of the reactor. The methyl chloride in lines 40 and 44 pass into jets 62 and 64 and in combination with jet 50 to cause the coarser silicone particles as mentioned previously in accordance with Dotson to be comminuted against each other. It should be noted that the reactor area is filled with copper particles, suitably the copper particles through line 70. The transfer coil 80 removes heat from the reactor so as to keep the temperature of the reactor within the range of 250° to 350° C. In accordance with the instant invention, silicon fines and product are removed from the reactor through line 82 and passed into cyclone 84 where in the coarser particles are returned through line 88. The silicon particles are returned through line 88. Silicon particles of less than 40 microns in size in average diameter as well as chlorosilane product is taken out through line 90 and passed to a second cyclone 94. From second cyclone 94 there is taken off through line 100 organosilane product and some particles of silicone and copper, silicon particles predominately 2 or 3 microns in diameter size and organic chloride. The silicon fines and silicon copper fines as disclosed previously are separated out in second cyclone 94 and passed through line 102 valve 104 through line 106 into receiving hopper 110 and are taken through line 122, valve 118 line 120 into transfer hopper 124. From transfer hopper 124 they are passed from line 130, valve 132 to line 134. In accordance with the disclosure of the instant case the fines after this treatment could be returned to the reactor. Thus the abraiding of the particles, and by particles or fines it is meant particles of less than 40 microns in average diameter down to 1 or less microns in average diameter. Such particles are abraided in the instant invention by being passed to the first cyclone 84 to the second cyclone 94 to the receiving hopper 110 to the transfer hopper 124. Such transfer and separation of the particles constitute sufficient abraiding of the particles such that they can be reused in reactor. A small stream of the fines in line 134 are taken out as waste in line 136. This waste or portion of fines constitutes from 10 to 40 percent of the fines. This bleeding of a portion of fines on line 136 is needed to bleed the impurities from the silicone fines such impurities as iron and magnesium comminuted with the virgin silicone metal and also to rid the system of that small amount of unrecoverable poisoned silicon and silicon copper fines material. The rest of the fines can then be recycled from line 134 through line 138 for an additional abraiding treatment of the fines as outlined in block 140 which can be ball milling of the fines and then passing them through line 142 into feed hopper 14 so as to feed along with virgin silicon particles entering through lines 12 into feed hopper 14 into reactor 10.

It should be noted that the additional treatment of fines of block 140 and step 140 need not be used in accordance with the instant invention. It is preferably utilized to further abraid the particles so that they are more active when they are recycled into the reactor.

Figure 2:
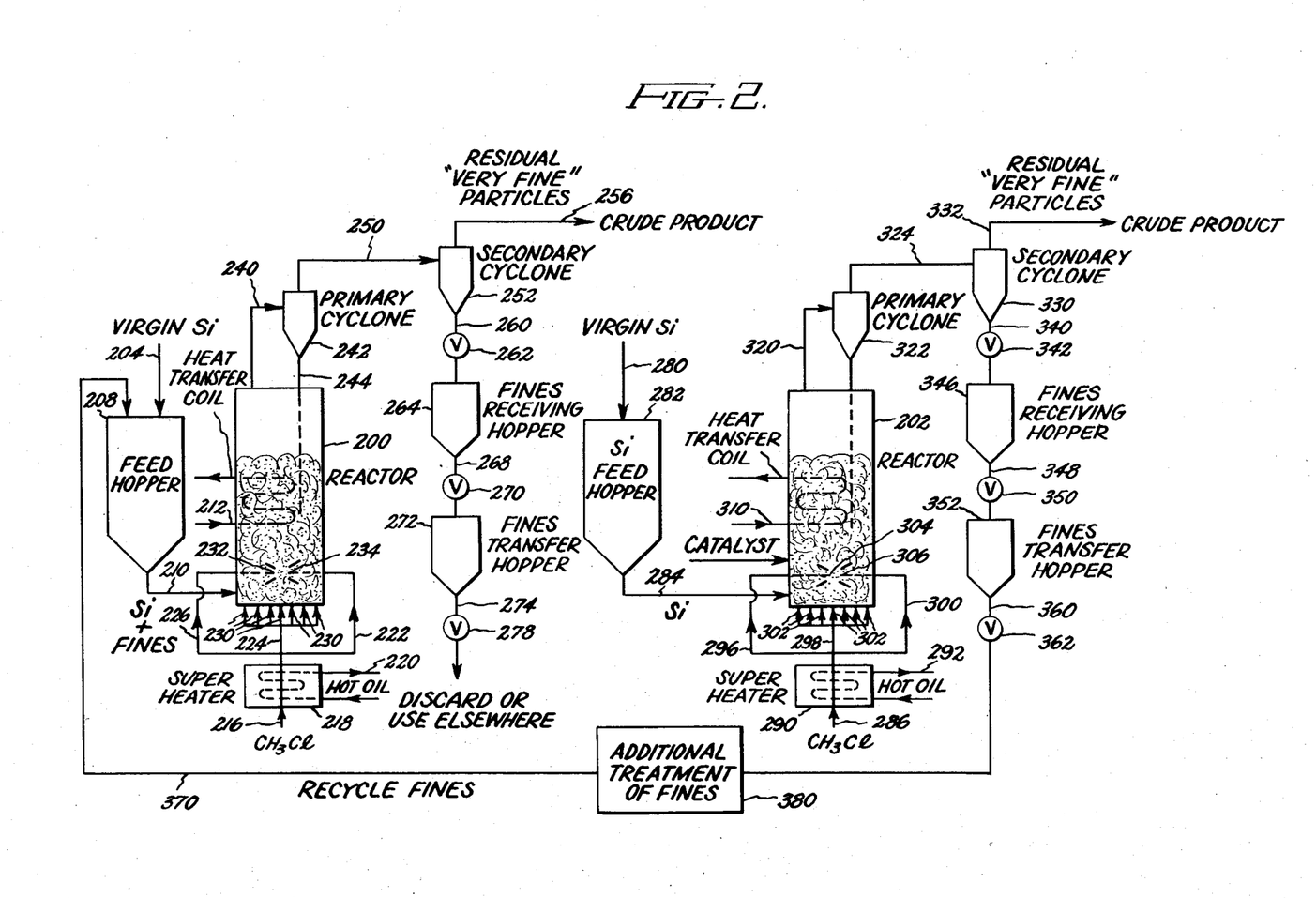
FIG. 2 is a schematic diagram of preferred process of the instant case as applied to two silicone reactors.

The most preferred process of the instant case is disclosed in FIG. 2, where two reactors 200 and 202 are utilized. Two reactors are preferred in silicone plants such that if one ceases to function for one reason or another the other can still produce silicon materials to keep most of the process lines in the plant open or working. In accordance, with the disclosure of FIG. 2 virgin silicon particles are feed through line 204 into feed hopper 208 and then line 210 into reactor 200. Reactor 200 has heat transfer coil 212 to remove heat from the reactor so as to maintain the temperature in the reactor from 250° to 350° C. As disclosed with FIG. 1 methyl chloride or another organo chloride is feed into line 216 through superheater 218 which is heated by hot oil passing through line 220 the organo chloride or methyl chloride passes through line 216 then lines 222, 224, 226 through jets 230 and jets from lines 226 to 232 and from line 222 to 234 so as to comminuting the coarser particles introduced through line 210, in accordance with the disclosure of Dotson. Organochlorosilane product along with silicon particles are removed through lines 40 into primary cyclone 242 wherein the coarser particles are returned to the reactor through line 244 and wherein the organochlorosilane products along with silicon fines of the instant invention is passed on through line 250 into second cyclone 252. Organochlorosilane product along with such very fine particles predominately less than 2 or 3 microns in size as well as organic chloride is removed through line 256. The silicone fines of the invention are collected in secondary cyclones 252 and then passed through line 260 and valve 262 to receiving hopper 264. After a sufficient amount has accumulated in the receiving hopper 267, the fines are passed through lines 228 and valve 270 into fines transfer hopper 272. They are then passed from transfer hopper 272 through line 274 valve 278 to a dumping place where they are discarded. Now to the second reactor 202; virgin silicon material particles pass through line 280 into feed hopper 282. From feed hopper 282 the silicon passes through line 284 to the bottom of reactor 202. At the bottom of reactor 202 organic chloride or methyl chloride passes through line 286 after being superheated in superheater 290 which is heated by hot oil coil 292 into lines 296, 298, and 300. The organo chloride from lines 286, 298 passes into jets 302 and organic chloride from lines 296 and line 300 from jets 304 and 306 respectfully. The near sonic velocity of the methyl chloride passing through these jets of 302, 304 and 306 causes comminution of the silicon particles entering the reactor through lines 284 or as was the case in reactor 200.

As was the case with the reactor in FIG. 1 any coarse silicon particles that happens to find it way from the top part of the reactor to the lower part of the reactor is comminuted. The heat transfer coil 310 takes out heat from the reactor. The reactor is usually maintained at a temperature of 250° to 350° C. Superheater 290 heats the organo chloride passing into through lines 286 and passing into the reactor through lines 296, 298 and 300 o a temperature of 250° to 300° C. From reactor 202 passes the product as well as the silicon fines of the instant invention through line 320 as well as other coarser silicone particles. The coarse products are returned to reactor 202 through line 34. The organochlorosilane product organic chloride and silicon fines of the instant invention and coarse silicon are rejected in primary cyclone 322 and from primary cyclone 322 through line 324 into secondary cyclone 330. From secondary cyclone 330 to line 332 there passes organochlorosilane product, and some of predominately very fine particles of predominantly 2 or 3 microns in size and organic chloride. The silicon fines of the instant case are collected as secondary cyclone 330 and then are passed through line 340 and valve 342 into receiving hopper 346. From receiving hopper 346 after sufficient silicon fines of the instant case are collected they are passed through line 348 valve 350 into transfer hopper 352 and from transfer hopper 352 after a sufficient amount has been collected of the silicon fines (and by silicon fines it is meant of less than 40 microns in average diameter, particles of silicon and copper silicon with a micron particle size of approximately 10 microns) are then passed through lines 360 and valve 362 back into line 370 into feed hopper 208 for feeding along with virgin silicon particles entering through line 204 into feed hopper 208 and then mixing and being feed through line 210 into the first reactor, reactor 200. It should be noted that it is preferred and in the preferred process of the instant case the fines from transfer hopper 352 are passed through valve 362 and line 370 back into feed hopper 208 for feeding to reactor 200. However, as an additional improvement over the preferred process of the instant case, the fines from transfer hopper 352 may be passed into an additional treatment of the fines as shown in Box 380. This additional treatment of the fines may be preferably ball milling of the fines of the instant case before they are fed through 370 back into feed hopper 208. It should be noted that it is not necessary to use this additional abrading treatment of the fines of 380 which is preferably ball milling or passing through a screw conveyor. However, the additional treatment can be carried out if it is desired to activate the silicon fines even further then is done by the passage to the cyclones and the receiving hoppers.

It should be noted that the passage of the silicon fines of the instant case through the cyclones and the receiving hoppers, is sufficient to abrade the surface of the silicon fines of the instant case so that the fines may be recycled into the first reactor without further treatment. However, to activate such particles even further, in a more preferred embodiment the particles will be subjected to additional abrading treatment such as in a ball mill or passing through a screw conveyor or by some other abrading treatment discussed above.

Figure 3:
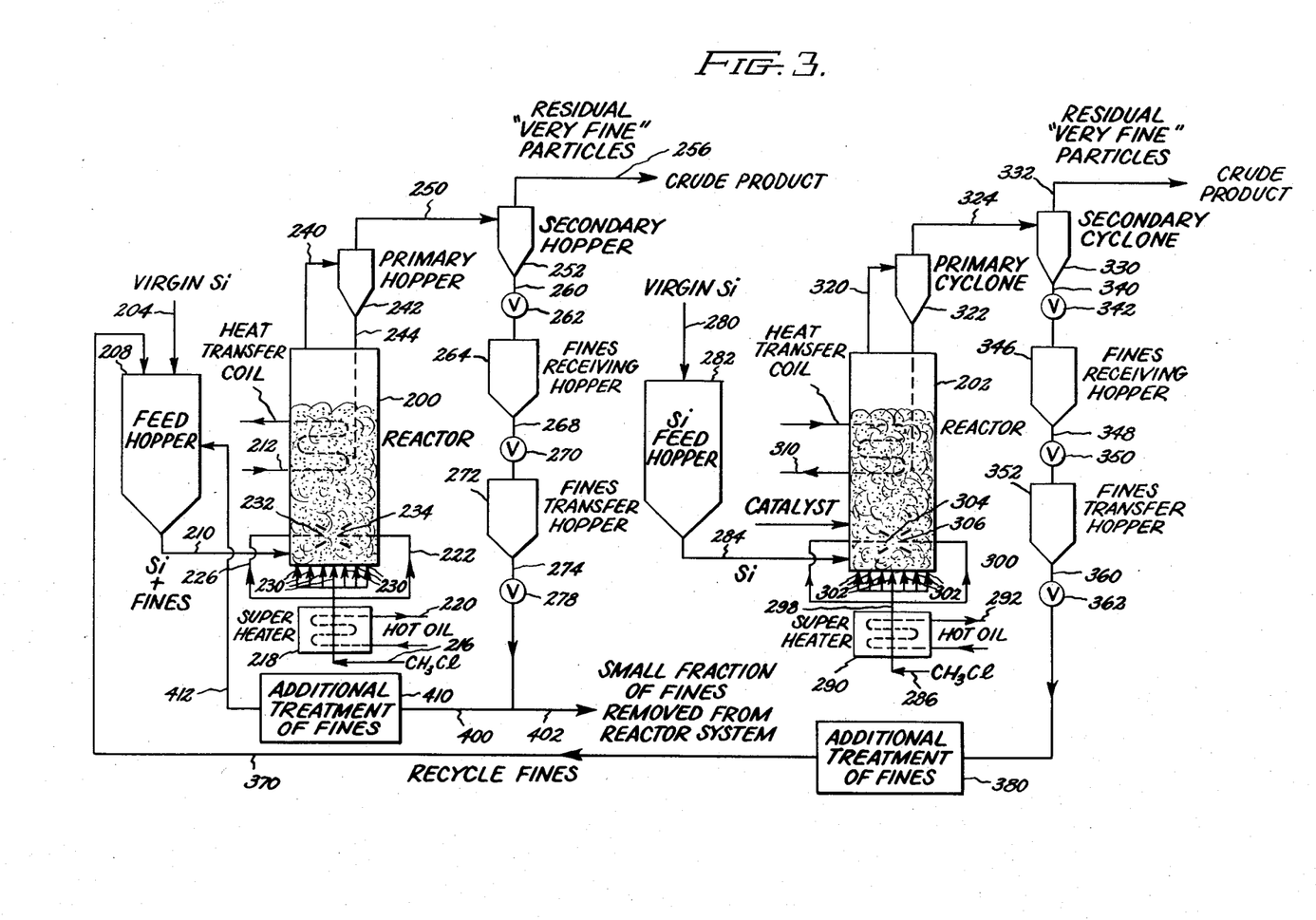
FIG. 3 is a schematic diagram of an alternate embodiment of the preferred process of FIG. 2.

FIG. 3 is a modification of the process of FIG. 2 and is slightly less preferred. In FIG. 3 wherein the same numbers have been adopted as FIG. 2 for the same lines, the fines of the instant case from reactor 202 are passed to line 278 into line 400. A portion of the fines is taken out as waste material, through line 402 so as to get rid of impurities in the virgin silicon material to the reactors 200 and 202 and also so as to ride of that small portion of the spent silicon material and silicon copper materials that cannot be used any further. Usually this stream that is taken out in line 402 as FIG. 1 may vary from 10 to 40 percent of total stream of silicon fines in lines 278. The rest of the stream of fines in line 278 is then passed through line 400 into an additional treatment fines as disclosed in block 410 which may be a ball milling or it may be a screw conveyor abrading treatment or another one of the abrading treatments discussed previously. It should be noted that there does not have to utilized an additional abrading treatment 410 to make the silicon fines more active. Preferably the silicon fines are further treated by an additional abrading treatment other than forcing through the primary and secondary cyclone 272 and 252 and to receiving hopper 274 and transfer hopper 272. After being passed through additional abrading treatment of fines steps 410 this stream of silicon fines is passed through line 412 into feed hopper 208 where it is feed along with virgin silicon material through line 210 to reactor 200. By utilizing this alternate process disclosed in FIG. 3 the fines are from reactor 200 are not discarded and some use is made of these fines by their being recycled and being utilized in reactor 200.

As a further alternative embodiment of the instant case, the embodiment of FIG. 2 can be taken and the fines from line 278 can be recycled after the usual waste stream bleed and a preferred additional abrading treatment of fines into feed hopper 282 so that the recycled fines can be fed to lines 284 along with virgin silicon particles to reactor 202.

It should be noted that the original preferred embodiment as shown in FIG. 2 was disclosed as such because in reactor 202 was generated 2/2 of the total fines in both reactor systems. Accordingly, it was more economical to recycle the fines of reactor 202 then the fines of reactor 200 in actual commercial application. However, as pointed out this may not be the case and further the fines from reactor 200 may be recycled to be utilized in reactor 200 as disclosed in FIG. 3. In a further embodiment not shown in any drawing the fines from reactor 200 may be recycled after the usual waste bleed stream and additional abrading treatment of the stream to be utilized in reactor 202 so as to make a more fully utilization of the fines in accordance with the invention of the instant case. It should also be noted that the above process for treating the fine was shown in a continuous process in FIGS. 1, 2, 3. It is, of course, obvious that in a semi-batch process that the same principles would apply as disclosed and the process of FIGS. 1, 2, 3, would simplier to implement. A batch process would be even simpler to implement in accordance with the instant disclosure but it would be less economical than the semi-continuous. Accordingly, it is preferred to run the production of organochlorosilane in a continuous manner in the process of FIGS. 1, 2, 3 and there may be utilized to carry out the process two reactors so as to abraid and recycle the fines so that they be reutilized either in reactor 200 on reactor 202, as the case may be and dependent on which reactor produces most fines. It should be noted that an additional benefit of the recycle of the fines in FIG. 2 is that reactor 200 is runned at 20° to 30° C. lower temperature than reactor 202 and upper catalyst does not have to be introduced into reactor 200. It should also be noted as referred to in the drawings some of the particles of less than 2 or 3 microns in size will go out with the organochlorosilane product but some of the particles of less than 2 or 3 microns in size will go with the fines of 40 microns or less which are recycled and which will be abraided in accordance with the instant invention.

The average particle size of most of the fines that are claimed in accordance with the instant invention and which are less than 40 microns in diameter is probably 5–10 microns in diameter.

It should also be appreciated that the present process can be implemented with more than two reactors in line and as many as necessary to run a particular silicon plant. The basis of the instant invention is not in the number of reactors utilized but in the abraiding of silicon fines particles defined in the instant case so as to remove the poisoning surface contaminant from the particles so that it may be reutilized in the basic silicone reaction to produce further diorganodichlorosilanes without exceeding the maximum T/D value permissible. It should be appreciated that utilizing the process of the instant case it is possible to utilize so much of the silicon of the virgin silicon particles that is submitted to the reactor that only seven percent to as low as five percent of silicon that is introduced to the reactor is lost as waste from the reactor system. The examples given below are given for the purpose of illustrating the present invention, and they are not given for any purpose of setting boundaries or limited to the instant invention. All parts of the examples are by weight.

EXAMPLE 1

The objective of this experiment was to learn the effect of stirring (and thus abrasion) on the T/D value. The experiment was conducted using a 1" inside diameter cylindrical reactor which was fitted with a helical ribbon stirrer. The helical ribbon was about 3/16" wide and attached to a central drive shift through a series of spokes. As the drive shaft rotated, the ribbon provided a lifting action to the particles near the wall and allowed them to move toward the bottom along the center shaft. This motion also caused direct particle-to-particle abrasion.

A charge composed of 20 grams of fines from a commercial reactor and 56 grams of ground virgin silicon was placed in the reactor. The system was brought to temperature under a low flow of nitrogen gas. When it stabilized at 300° C., the methyl chloride flow was started at 11 grams per hour. The methyl chloride entered the bottom of the reactor at a sufficiently low flow rate so that particle fluidization was negligible. This rate was maintained throughout the experiment.

| % Si Utilization | Normalized Rates* | | | |
|---|---|---|---|---|
| | Di | Tri | T/D | |
| 1.0 | 0.26 | 0.09 | 0.35 | ↑ |
| 6.0 | 0.23 | 0.06 | 0.26 | Stirrer |
| 15.0 | 0.30 | 0.06 | 0.20 | on at |
| 17.5 | 0.27 | 0.06 | 0.22 | 60 RPM |
| 20.3 | 0.21 | 0.08 | 0.38 | ↓ |
| 23.5 | 0.15 | 0.06 | 0.40 | ↑ |
| 25.5 | 0.16 | 0.05 | 0.31 | Stirrer |
| 28.8 | 0.10 | 0.03 | 0.30 | Off |
| 29.6 | 0.10 | 0.04 | 0.40 | ↓ |
| 32.0 | 0.09 | 0.04 | 0.44 | ↓ |
| 34.5 | 0.11 | 0.05 | 0.45 | ↑ |
| 37.4 | 0.07 | 0.04 | 0.57 | Stirrer |
| 38.2 | 0.11 | 0.05 | 0.45 | on |
| 39.7 | 0.14 | 0.04 | 0.28 | 60 RPM |
| 40.2 | 0.19 | 0.05 | 0.26 | ↓ |

*"Normalized rate" means grams of that component produced per hour per gram of fines remaining in the reactor at that time.
**"% Si Utilization" refers to the silicon contained in the 20 grams of fines charged to the reactor.

It should be noted that during the first stage of the experiment, when the stirrer was operating, there was a significant decrease in the T/D value. When the stirrer was stopped the T/D value started to rise since there was no abrasive action to remove the deleterious surface contamination that forms. Upon starting the stirrer the T/D value again was observed to fall due to the removal of surface contamination.

EXAMPLE 2

A commercial size reactor was operated under conditions so that the T/D was very high (approximately 2.0). (At this time there was only a very low removal rate for fines from the reactor due to a low velocity of vapor through the reactor). A sample of bed powder was removed from the reactor and placed in a 1-inch laboratory reactor with a stirrer as described in Example No. 1.

The table shown below contains the data on the observed T/D value as a function of time.
Change: 76.1 g. of bed powder
Temperature: 300° C.
Methyl Chloride Flow Rate: 1 μg/hr.

| Time | Total Si Consumed, g | T/D |
|---|---|---|
| 0 | 0 | Started CH$_3$Cl flow |
| 18 | — | First product observed |
| 44 | 0.17 | 1.8 |
| 109 | 1.18 | 0.54 |
| 157 | 2.76 | 0.29 |
| 217 | 4.38 | 0.19 |
| 277 | 6.16 | 0.16 |
| 337 | 7.98 | 0.14 |
| 399 | 9.79 | 0.13 |
| 447 | 11.38 | 0.13 Run Discontinued |

There are a number of conclusions to be drawn from these data. It should be noted that the initial T/D value corresponds to the value observed in the commercial reactor at the time the sample was taken. Also, the laboratory reactor T/D value decreases continuously to a final value of 0.13. This is in sharp contrast to the performance of the commercial reactor wherein the T/D continued to increase. The difference between these two observations is due to the physical abrasion between particles in direct continuous contact in the laboratory reactor and the lack of such abrasion in the fluid bed reactor.

EXAMPLE 3

Fines were collected from one commercial reactor under normal operating conditions such that the T/D was 0.15±0.2. The collected fines were then used as the feed to a second commercial reactor. The performance of the second reactor is indicated in the table shown below. It should be noted that no additional catalyst was required for the second reactor during the time period fines constituted the feed, in total or in part.

TABLE

| Day | Feed Composition | Catalyst Addition | Average T/D |
|---|---|---|---|
| 1 | 100% New Si | Yes | 0.10 |
| 2 | 100% Fines | No | 0.13 |
| 3 | 50% Fines/100% New Si | No | 0.17 |
| 4 | 50% Fines/100% New Si | No | 0.17 |
| 5 | 50% Fines/100% New Si | No | 0.18 |
| 6 | 50% Fines/100% New Si | No | 0.18 |
| 7 | 50% Fines/100% New Si | No | 0.22 |
| 8 | 50% Fines/100% New Si | No | 0.25 |
| 9 | 50% Fines/100% New Si | No | 0.30 |
| 10 | 50% Fines/100% New Si | No | 0.29 |
| 11 | Run Discontinued | | |

The data shown in the table clearly demonstrate that fines can be utilized in a commercial reator system, over extended time periods, while maintaining the T/D value in the acceptable range.

During the time the fines were collected from the first reactor the silicon feed rate to that reaction was the normal 70,000 to 75,000 pounds per day. All of the fines collected from the first reactor were fed to the second reactor along with approximately 25,000 pounds of virgin silicon. The fines collected from the second reaction were approximately 8000 to 9000 pounds per day. These fines were approximately 75 percent silicon along with contaminats such as carbon, iron, aluminum, and copper. Thus the silicon in the fines was approximately 6,000 to 7,000 pounds per day (0.75×9000−6750). Considering the two reactors together as an integrated system, the total virgin silicon fed per day was 95,000 to 100,000 pounds, and the silicon discarded from the second reactor per day was 6000 to 7000 pound. In total, the silicon collected as fines and discarded from the system was approximately 7 percent of the silicon fed to the system.

I claim:

1. A process for treating the particles in a silicone reactor where an organic chloride where the organic is a monovalent hydrocarbon radical is reacted with particles of silicon in the presence of copper comprising (a) removing particles selected from silicon particles and particles of silicon and copper from said reactor of less than 40 microns average diameter particle size; (b) abraiding said particles to remove the surface coating of said particles; and (c) returning said particles to the reactor.

2. The process of claim 1 wherein said particles are removed to maintain the T/D ratio less than 0.35 where T is organotrichlorosilane and D is diorganodichlorosilane wherein the organo is a monovalent hydrocarbon radical.

3. The process of claim 1 wherein the reactor is operated at atmospheric to 60 psig and at a temperature of 250° to 350° and the particles are abraided at a room temperature to 300° C.

4. The proess of claim 1 wherein the particles are abraided in an atmosphere of moisture free-air.

5. The process of claim 1 wherein the particles are abraided by ball milling.

6. The process of claim 1 wherein the particles are abraided by passing through a screw conveyor.

7. The process of claim 1 wherein the particles are abraided by tumbling with coarser silicon.

8. The process of claim 1 wherein the particles are abraided by (1) passing the particles through to a first cyclone which separates out the particles of greater than 40 micron average diameter and these coarser particles are returned to the reactor, (2) transferring the fines particles of less than 40 microns in average diameter size to a second cyclone which separates the product from the fines, (3) sending the less than 40 microns average diameter particles fines to a receiving hopper, (4) transmitting the fines to a transfer hopper, (5) sending the fines to a feed hopper and (6) then passing the fines back to the reactor.

9. The process of claim 8 wherein a portion of the fines in step (5) are disposed from the system to get rid of wasted silicon materials and impurities.

10. The process of claim 9 wherein the wasted portion of the fines that is disposed is about 10% to 40% by volume.

11. The process of claim 10 wherein the coating that is removed from the particles is carbon containing contaminant.

12. A process for treating the particles of less than 40 microns in average diameter in the silicone reactor where organochloride is reacted with silicon particles and silicon-copper particles to produce organo chlorosilanes where organo is a monovalent hydrocarbon radical comprising (a) removing particles selected from silicon particles and particles of silicon and copper from the reactor and passing them to a first cyclone wherein the first cyclone separates particles of 40 microns in diameter or higher, and returns them to the reactor (b) abraiding said particles of less than 40 microns size average diameter by transferring the particles through a second cyclone wherein said second cyclone separates the chlorosilane product from fine particles and removes them with the product and are passed out the second cyclone, (c) transmitting the fines particles of 40 microns or less than average diameter to a receiving hopper, (d) sending the fines from said receiving hopper to a transfer hopper, (e) passing a portion of the fines in the transfer hopper to be discarded as waste so as to get rid of impurities and spent silicon particles, (f) transferring the rest of the fines to a feed hopper; (g) passing the particles or fines from a feed hopper back into the reactor wherein the reactor is operated at temperatures of 250° to 350° C. where the weight ratio of triorganochlorosilane to diorganochlorosilane in the reactor product does not exceed 0.35

13. A process for treating particles of an average diameter of less than 40 microns from silicone reactors wherein the silicone reactors have reacted therein organochloride with silicon particles and copper and silicone particles to produce organo chlorosilanes where the organo is a monovalent hydrocarbon radical comprising (a) passing from a first feed hopper silicon metal particles and copper catalyst particles into a first reactor; (b) removing the particles from the first reactor into a first cyclone so as to separate particles of 40 microns average diameter size and higher and returning them to the reactor (c) abraiding fines particles of less than 40 microns average diameter size by passing them to a secondary cyclone along the with chlorosilane product (d) passing product along with some fines particles as produced from the second cyclone (e) passing the fines particles of less than 40 micron average diameter or less to a first receiving hopper from said second cyclone, (f) transferring said fines to a first transfer hopper, (g) transmitting said fines to a second feed hopper along with virgin silicon particles, (h) transferring said fines from said second feed hopper along with virgin silicon particles and organo chloride to a second reactor, (i) removing a product stream from said second reactor and passing it to a third cyclone (j) returning particles of 40 microns or more average diameter size back to the second reactor from said third cyclone, (k) transferring chlorosilane product as well as particles of less than 40 microns in size from said third cyclone and abraiding fines particles of less than 40 microns average diameter size in said third cyclone by passing them to a fourth cyclone, (l) removing chlorosilane product from the fourth cyclone along with some fines particles as a product stream (m) transmitting said fines particles of less than 40 microns average diameter size into a second receiving hopper (n) sending fines from said second receiving hopper into a second transfer hopper, and (o)

transmitting said fines from said second transfer hopper to waste disposal.

14. The process of claim 13 wherein in step (g) said fines are passed to additional abraiding treatment before being passed to the second feed hopper.

15. The process of claim 14 wherein the additional abraiding treatment comprises ball milling the fines.

16. The process of claim 14 wherein the additional abraiding technique comprises passing the fines through a screw conveyor.

17. The process of claim 17 wherein the additional abraiding of the particle comprises tumbling the fines with coarser silicon.

18. The process of claim 17 wherein in the first reactor the reaction is carried out at about 275° to 320° C. to produce the chlorosilanes product and wherein the second reactor the reaction is carried out at a temperature of 250° to 300° C. to produce the chlorosilanes product.

19. The process of claim 14 wherein the T/D weight ratio in the product does not exceed 0.35 in either the first or second reactor with T being organotrichlorosilane and D is diorganochlorosilane.

20. The process of claim 13 further comprising taking the fines stream from the second transfer hopper and discarding a portion of the particles as waste to get rid of impurities and spent silicon particles and then transferring the remaining portion of the fines stream to an additional abraiding treatment of the fines and then transmitting said fines stream after having been treated into a second feed hopper for passing into said second reactor along with the virgin silicon particles.

21. The process of claim 13 further comprising taking the fines stream from said second transfer hopper discarding a portion of said fines stream so as to remove impurities and spent silicon material from the system and transferring the rest of said fines stream from the second transfer hopper to an additional abraiding treatment and passing the fines after said treatment said first feed hopper along with virgin silicon material for feeding into said first reactor.

22. The process of claim 20 wherein the additional abraiding treatment comprises ball milling the fines.

23. The process of claim 20 wherein the additional abraiding treatment comprises passing the fines through a screw conveyor.

24. The process of claim 20 wherein the additional abraiding treatment comprises tumbling the fines with coarser silicon.

25. The process of claim 21 wherein the additional abraiding treatment of the fines comprises ball milling the fines.

26. The process of claim 21 wherein the addition abraiding treatment comprises passing the particles through a screw conveyor.

27. The process of claim 21 wherein the additional abraiding treatment comprises tumbling the fines with coarser silicon and then feeding the fines into the first feed hopper.

28. The process of claim 20 wherein the additional abraiding treatment is carried out in an atmosphere of moisture-free air.

29. The process of claim 21 wherein the additional abraiding treatment is carried out in an atmosphere of moisture-free air.

* * * * *

UNITED STATES PATENT AND TRADEMARK OFFICE
CERTIFICATE OF CORRECTION

PATENT NO. : 4,281,149
DATED : July 28, 1981
INVENTOR(S) : Ray W. Shade

It is certified that error appears in the above—identified patent and that said Letters Patent is hereby corrected as shown below:

Column 15, line 25, after "chloride" insert -- , -- .

Column 15, line 26, after "radical" insert -- , -- .

Column 15, line 31, "abraiding" should read -- abrading --

Signed and Sealed this

Eighth Day of December 1981

[SEAL]

Attest:

*Attesting Officer*

GERALD J. MOSSINGHOFF
*Commissioner of Patents and Trademarks*